United States Patent [19]

Sih

[11] 4,275,233

[45] Jun. 23, 1981

[54] 19-HYDROXY-19-METHYL-13,14-DIHYDRO-PG$_2$ COMPOUNDS

[75] Inventor: John C. Sih, Kalamazoo, Mich.

[73] Assignee: The Upjohn Company, Kalamazoo, Mich.

[21] Appl. No.: 133,205

[22] Filed: Mar. 24, 1980

Related U.S. Application Data

[62] Division of Ser. No. 25,878, Apr. 2, 1979, abandoned.

[51] Int. Cl.$^3$ ............................................ C07C 177/00
[52] U.S. Cl. ..................................... 562/503; 560/121; 260/408; 260/410; 260/410.5; 260/410.9 R; 260/413
[58] Field of Search ...................... 260/408, 410, 410.5, 260/410.9 R, 413; 560/121; 562/503

[56] References Cited

U.S. PATENT DOCUMENTS 4,054,595  10/1977  Marx .................................... 560/121

Primary Examiner—Robert Gerstl
Attorney, Agent, or Firm—Robert A. Armitage

[57] ABSTRACT

The present invention provides novel 19-hydroxy-19-methyl-13,14-dihydro-PG$_2$ compounds, methods for their preparation and pharmacological use for the induction of prostaglandin-like effect.

2 Claims, No Drawings

19-HYDROXY-19-METHYL-13,14-DIHYDRO-PG$_2$ COMPOUNDS

DESCRIPTION

Cross Reference to Related Applications

The present application is a division of Ser. No. 025,878, filed 2 Apr. 1979 now abandoned.

BACKGROUND OF THE INVENTION

The present invention relates to novel prostaglandin analogs. Particularly, these compounds are analogs of the prostaglandins wherein the C-19 position is substituted by hydroxy, i.e., 19-hydroxy-19-methyl-PG compounds. Most particularly, the present invention relates to novel 19-hydroxy-19-methyl-13,14-dihydro-PG$_2$ compounds, a disclosure of the preparation and use of which is incorporated here by reference from U.S. Ser. No. 025,899, filed 2 Apr. 1979 now U.S. Pat. No. 4,228,104.

PRIOR ART

Prostaglandin analogs exhibiting hydroxylation in the 19-position are known in the art. See, for example, U.S. Pat. No. 4,127,612, Sih, J. C., Prostaglandins 13:831 (1977) and U.S. Pat. Nos. 3,657,316, 3,878,046, and 3,922,297. See also the additional references cited in U.S. Ser. No. 025,878.

SUMMARY OF THE INVENTION

The present invention particularly provides: a compound of the formula

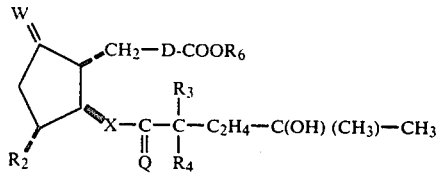

wherein D is
 (1) cis-CH=CH—CH$_2$—(CH$_2$)$_g$—CH$_2$—, or
 (2) cis-CH=CH—CH$_2$—(CH$_2$)$_g$—CF$_2$—,
wherein g is zero, one, two, or three;
wherein Q is α-OH:β-R$_5$ or α-R$_5$:β-OH, wherein R$_5$ is hydrogen or methyl;
wherein R$_6$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive,
 (g) —(p—Ph)—CO—CH$_3$,
 (h) —(p—Ph)—NH—CO—(p—Ph)—NH—CO—CH$_3$,
 (i) —(p—Ph)—NH—CO—(p—Ph),
 (j) —(p—Ph)—NH—CO—CH$_3$,
 (k) —(p—Ph)—NH—CO—NH$_2$,
 (l) —(p—Ph)—CH=N—NH—CO—NH$_2$,
 (m) β-naphthyl,
 (n) —CH$_2$—CO—R$_{28}$,
wherein (p—Ph) is para-phenyl or inter-para-phenylene.

wherein R$_{28}$ is phenyl, p-bromophenyl, p-biphenylyl, p-nitrophenyl, p-benzamidophenyl, or 2-naphthyl, or
 (o) a pharmacologically acceptable cation;
wherein R$_2$ is hydrogen, hydroxyl, or hydroxymethyl;
wherein R$_3$ and R$_4$ are hydrogen, methyl, or fluoro, being the same or different, with the proviso that one of R$_3$ and R$_4$ is fluoro only when the other is hydrogen or fluoro;
wherein W is oxo, methylene, α-OH:β-H, or α-H:β-OH; and
wherein X is —CH$_2$CH$_2$—.

With regard to the divalent the substituents described above (e.g., Q) these divalent radicals are defined as α-R$_i$:β-R$_j$, wherein R$_i$ represents the substituent of the divalent moiety in the alpha configuration with respect to the ring and R$_j$ represents the substituent of the divalent moiety in the beta configuration with respect to the plane of the ring. Accordingly, when Q is defined as α-OH:β-R$_5$, the hydroxy of the Q moiety is in the alpha configuration, i.e., as in the natural prostaglandin, and the R$_5$ substituent is in the beta configuration.

Specific embodiments of the present invention include:
19-hydroxy-19-methyl-13,14-dihydro-PGF$_2$α.

The compounds of the present invention are particularly useful for inducing prostaglandin-like biological effects, as is described in U.S. Ser. No. 025,878. Uses of compounds in accordance with the present invention include, therefore, anti-asthmatic indications.

I claim:
1. A compound of the formula

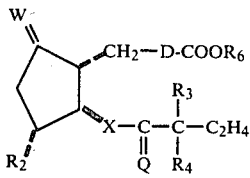

wherein D is
 (1) cis—CH=CH—CH$_2$—(CH$_2$)$_g$—CH$_2$—, or
 (2) cis—CH=CH—CH$_2$—(CH$_2$)$_g$—CF$_2$—,
wherein g is zero, one, two, or three;
wherein Q is α-OH:β-R$_5$ or α-R$_5$:β-OH, wherein R$_5$ is hydrogen or methyl;
wherein R$_6$ is
 (a) hydrogen,
 (b) alkyl of one to 12 carbon atoms, inclusive,
 (c) cycloalkyl of 3 to 10 carbon atoms, inclusive,
 (d) aralkyl of 7 to 12 carbon atoms, inclusive,
 (e) phenyl,
 (f) phenyl substituted with one, 2, or 3 chloro or alkyl groups of one to 3 carbon atoms, inclusive,
 (g) —(p—Ph)—CO—CH$_3$,
 (h) —(p—Ph)—NH—CO—(p—Ph)—NH—CO—CH,
 (i) —(p—Ph)—NH—CO—(p—Ph),
 (j) —(p—Ph)—NH—CO—CH$_3$,
 (k) —(p—Ph)—NH—CO—NH$_2$,
 (l) —(p—Ph)—CH=N—NH—CO—NH$_2$,
 (m) β-naphthyl,
 (n) —CH$_2$—CO—R$_{28}$,
wherein (p—Ph) is para-phenyl or inter-para-phenylene, wherein $R_{28}$ is phenyl, p-bromophenyl, p-biphenylyl, p-nitrophenyl, p-benzamidophenyl, or 2-naphthyl, or (o) a pharmacologically acceptable cation;

wherein $R_2$ is hydrogen, hydroxyl, or hydroxymethyl;

wherein $R_3$ and $R_4$ are hydrogen, methyl, or fluoro, being the same or different, with the proviso that one of $R_3$ and $R_4$ is fluoro only when the other is hydrogen or fluoro;

wherein W is oxo, methylene, $\alpha$-OH:$\beta$:H, or $\alpha$-H:$\beta$-OH; and wherein X is —$CH_2CH_2$—.

2. 19-hydroxy-19-methyl-13,14-dihydro-$PGF_{2\alpha}$, a compound according to claim 1.

* * * * *